(12) United States Patent
Mizumoto

(10) Patent No.: US 11,458,047 B2
(45) Date of Patent: Oct. 4, 2022

(54) TRUNKS-TYPE DISPOSABLE DIAPER

(71) Applicant: Daio Paper Corporation, Ehime (JP)

(72) Inventor: Yousei Mizumoto, Sakura (JP)

(73) Assignee: Daio Paper Corporation, Ehime (JP)

( * ) Notice: Subject to any disclaimer, the term of this patent is extended or adjusted under 35 U.S.C. 154(b) by 564 days.

(21) Appl. No.: 16/349,098

(22) PCT Filed: Nov. 22, 2017

(86) PCT No.: PCT/JP2017/041929
§ 371 (c)(1),
(2) Date: May 10, 2019

(87) PCT Pub. No.: WO2018/097158
PCT Pub. Date: May 31, 2018

(65) Prior Publication Data
US 2019/0274898 A1    Sep. 12, 2019

(30) Foreign Application Priority Data

Nov. 25, 2016 (JP) .............................. JP2016-229582

(51) Int. Cl.
*A61F 13/496*    (2006.01)
*A61F 5/44*    (2006.01)
(Continued)

(52) U.S. Cl.
CPC .......... *A61F 13/496* (2013.01); *A61F 5/4404* (2013.01); *A61F 13/49* (2013.01);
(Continued)

(58) Field of Classification Search
CPC ............ A61F 13/49009; A61F 13/4963; A61F 13/49019; A61F 13/496; A61F 2013/49088; A61F 13/4906; A61F 13/49017
See application file for complete search history.

(56) References Cited

U.S. PATENT DOCUMENTS

| | | | | |
|---|---|---|---|---|
| 2003/0097109 A1* | 5/2003 | Bruce | ............... | A61F 13/47236 604/385.01 |
| 2005/0148988 A1* | 7/2005 | Kinoshita | ............. | A61F 13/535 604/396 |
| 2009/0299319 A1* | 12/2009 | Takahashi | ......... | A61F 13/49019 604/385.25 |

FOREIGN PATENT DOCUMENTS

| | | |
|---|---|---|
| JP | H11-332911 | 12/1999 |
| JP | 2002-178428 | 9/2002 |

(Continued)

OTHER PUBLICATIONS

International Search Report, PCT/JP2017/041929, dated Dec. 19, 2017.

*Primary Examiner* — Susan S Su
(74) *Attorney, Agent, or Firm* — Andrus Intellectual Property Law, LLP

(57) ABSTRACT

A trunks-type disposable diaper is configured to prevent shrinkage in the width direction of an inner thigh contact portion and to prevent the wearing feeling and occurrence of a gap. A crossing position of a front around-leg elastic member and a back around-leg elastic member positioned closest to an edge of a leg opening is positioned at the same position in a width direction as a side edge of the narrowest portion of a narrower portion of an absorber or on the center side in the width direction, and a crotch portion does not have elastic members other than the front around-leg elastic member and the back around-leg elastic member.

10 Claims, 16 Drawing Sheets

(51) Int. Cl.
*A61F 13/493* (2006.01)
*A61F 13/494* (2006.01)
*A61F 13/49* (2006.01)

(52) U.S. Cl.
CPC .......... *A61F 13/493* (2013.01); *A61F 13/494* (2013.01); *A61F 13/4906* (2013.01); *A61F 13/49017* (2013.01); *A61F 13/49007* (2013.01)

(56) References Cited

FOREIGN PATENT DOCUMENTS

| | | |
|---|---|---|
| JP | 2002-273808 | 9/2002 |
| JP | 2006-230920 | 9/2006 |
| JP | 2007-61335 | 3/2007 |
| JP | 2007-167166 | 7/2007 |
| JP | 4439150 | 1/2010 |
| JP | 2010-82133 | 4/2010 |
| JP | 2010-227505 | 10/2010 |
| JP | 2012-24463 | 2/2012 |
| JP | 5208965 | 6/2013 |
| JP | 2013-188434 | 9/2013 |

\* cited by examiner

TRUNKS-TYPE DISPOSABLE DIAPER

CROSS-REFERENCE TO RELATED APPLICATIONS

This application is the U.S. national stage application of International Application PCT/JP2017/041929, filed Nov. 22, 2017, which international application was published on May 31, 2018, as International Publication WO 2018/097158 in the Japanese language. The International Application claims priority of Japanese Patent Application No. 2016-229582, filed Nov. 25, 2016. The international application and Japanese application are both incorporated herein by reference, in entirety.

TECHNICAL FIELD

The present invention relates to a trunks-type disposable diaper having improved fitting to the inner thigh.

BACKGROUND ART

An underpants-type disposable diaper generally includes an outer member, an inner member, and side seal portions. The outer member has a waist opening and a pair of leg openings and extends from a front waist opening edge to a back waist opening edge. The inner member is provided at least in a crotch portion of the outer member and includes an absorber. The side seal portions bond both sides on the front side and both sides on the back side of the outer member.

Further, as one form of the underpants-type disposable diaper, a trunks-type disposable diaper (also referred to as a one-quarter length form or a boxer type) having a pair of cylindrical leg portions surrounding root sides of the thighs. As a trunks-type disposable diaper having a simple structure in a cylindrical leg portion, a trunks-type disposable diaper is known in which a crotch portion of an outer member has a pair of inner thigh contact portions respectively extending to one side and the other side in the width direction of a circumscribed rectangle of an absorber, and a portion along edges of leg openings including these inner thigh contact portions is a pair of cylindrical leg portions surrounding root sides of the thighs (refer to, for example, Patent Literatures 1 to 5).

In such a trunks-type disposable diaper, like other types of underpants-type disposable diapers, in order to improve fitting to the body, various elastic members are fixed to an outer member in a stretched state. In particular, a front around-leg elastic member and a back around-leg elastic member are attached on both front and back sides of the outer member in a pattern of extending from one of side seal portions toward the center in the width direction along the edges of leg openings, crossing the center in the width direction towards the other leg opening, and extending along the other leg opening to the other side seal portion. The front around-leg elastic member and the back around-leg elastic member are important since those determines the fitting of cylindrical leg portions of a trunks-type disposable diaper.

In such a structure having the front around-leg elastic member and the back around-leg elastic member, when the front around-leg elastic member and the back around-leg elastic member are attached in a pattern in which at least one front around-leg elastic member and at least one back around-leg elastic member cross each other on both sides in the width direction of an intermediate region between an edge of one leg opening and an edge of the other leg opening, the around-leg elastic members are continuously present along leg openings, and there is an advantage that the fitting of the cylindrical leg portion is improved.

Also, in order to achieve both fitting to the leg and absorption amount, a trunks-type disposable diaper is also known in which an intermediate portion in the front-back direction of an absorber is a narrower portion having a narrower width than both front and back sides thereof (refer to, for example, Patent Literature 2).

CITATION LIST

Patent Literature

Patent Literature 1: JP 2006-230920 A
Patent Literature 2: JP 2007-061335 A
Patent Literature 3: JP 2010-82133 A
Patent Literature 4: JP 2010-227505 A
Patent Literature 5: JP 5208965 B2
Patent Literature 6: JP 4439150 B2

SUMMARY OF INVENTION

Technical Problem

However, it is not preferable if the crossing position of the front around-leg elastic member and the back around-leg elastic member is positioned outside the side edge of the narrower portion of the absorber, since the contraction force of the front around-leg elastic member and the back around-leg elastic member in the vicinity of the crossing position acts in the width direction, as a result of attracting the inner thigh contact portion to the center in the width direction, the length of the inner thigh contact portion is shortened, the wearing feeling is deteriorated, and a gap tend to occur with the skin.

Therefore, the main object of the present invention is to prevent shrinkage in the width direction of the inner thigh contact portion and to prevent the deterioration of the wearing feeling and the occurrence of the gap.

Solution to Problem

The representative aspects of the present invention that have solved the above problems will be described below.
<First Aspect>
In a trunks-type disposable diaper including an outer member having a waist opening and a pair of leg openings and extending from a front waist opening edge to a back waist opening edge, an inner member provided at least in a crotch portion of the outer member and including an absorber, and side seal portions that bond both sides on the front side and both sides on the back side of the outer member, the absorber has a narrower portion which is narrower than both front and back sides in an intermediate portion in a front-back direction, the crotch portion of the outer member has a pair of inner thigh contact portions which respectively extend to one side and the other side in the width direction from a circumscribed rectangle of the absorber, and portions along the edges of the leg openings including the inner thigh contact portions forms a pair of cylindrical leg portions surrounding root sides of the thighs, the front side of the outer member has one elongated front around-leg elastic member or a plurality of elongated front around-leg elastic members not crossing each other, the elastic member is attached in a pattern of extending from one of the side seal portions toward the center in the width direction along the edge of the leg opening, crossing the center in the width direction, extending toward the other leg opening, extending to the other side seal portion along the edge of the other leg opening, the back side of the outer member has one elongated back around-leg elastic member or a plurality of elongated back around-leg elastic members not crossing each other, the elastic member is attached in a pattern of extending from one of the side seal portions toward the center in the width direction along the edge of the leg opening, crossing the center in the width direction, extending toward the other leg opening, and extending to the other side seal portion along the edge of the other leg opening, and the front around-leg elastic member and the back around-leg elastic member are attached in a pattern in which at least one front around-leg elastic member and at least one back around-leg elastic member cross each other on both sides in the width direction of an intermediate region that is a region between the edge of one leg opening and the edge of the other leg opening.

A crossing position of the front around-leg elastic member and the back around-leg elastic member, positioned closest to the edge side of the leg opening is the same in the width direction position as the side edge of the narrowest part of the narrower portion or located on the further center side in the width direction, and the crotch portion does not have elastic members other than the front around-leg elastic member and the back around-leg elastic member.

(Function and Effect)

In the present aspect, the crossing position of the front around-leg elastic member and the back around-leg elastic member positioned closest to the edge side of the leg opening is located at the same position in the width direction as the side edge of the narrowest portion of the narrower portion or on the center side in the width direction, and also since the crotch portion does not have elastic members other than the front around-leg elastic member and the back around-leg elastic member, the contraction force of the front around-leg elastic member and the back around-leg elastic member does not easily attract the inner thigh contact portion to the center in the width direction. As a result, it is possible to suppress shortening of the length of the inner thigh contact portion, thereby making it possible to prevent deterioration of wearing feeling and occurrence of a gap.

<Second Aspect>

In the trunks-type disposable diaper according to the first aspect, the inner member bonded portion that is a region bonding the outer member and the inner member is provided only further to the center side in the width direction than the crossing position of the front around-leg elastic member and the back around-leg elastic member on both sides in the width direction in the intermediate region.

(Function and Effect)

In the present aspect, in the intermediate region between the edge of one leg opening and the edge of the other leg opening, the inner member bonded portion is provided only further to the center side in the width direction than the crossing position of the front around-leg elastic member and the back around-leg elastic member on both sides in the width direction, and the front around-leg elastic member and the back around-leg elastic member do not expand or contract together with the inner member. Therefore, the fitting is not deteriorated at a portion including a crossing position between the front around-leg elastic member and a back around-leg elastic member though the front around-leg elastic member and the back around-leg elastic member cross each other and are substantially continuous along the leg opening.

<Third Aspect>

In the trunks-type disposable diaper according to the first or second aspect, an interval between the edge of the leg opening and an elastic member closest to the edge of the leg opening in the direction orthogonal to a tangent to the edge of the leg opening in the front around-leg elastic member and the back around-leg elastic member is equal to or longer than 10 mm.

(Function and Effect)

When the interval between the edge of the leg opening and the elastic member closest to the edge of the leg opening is narrow, the crossing position of the front around-leg elastic member and the back around-leg elastic member is likely to be close to the edge of the leg opening. Therefore, it is difficult to position the crossing position further to the center side in the width direction than the side edge of the narrowest portion of the narrower portion in the absorber. Therefore, as in this aspect, it is preferable that this interval is 10 mm or more.

<Fourth Aspect>

In the trunks-type disposable diaper according to any one of first to third aspects, a non-stretchable region in which the front around-leg elastic member and the back around-leg elastic member are cut finely is provided to the center side in the width direction from the crossing position of the front around-leg elastic member and the back around-leg elastic member on both sides in the width direction.

(Function and Effect)

When the stretchable region including the front around-leg elastic member and the back around-leg elastic member is provided further to the center side in the width direction than the crossing position of the front around-leg elastic member and the back around-leg elastic member on both sides in the width direction, not only the wearing feeling is deteriorated due to contraction of the absorber in the width direction, but also the inner thigh contact portion is attracted toward the center in the width direction, and the length of the inner thigh contact portion may be shortened. Therefore, as in this aspect, it is preferable to form a non-stretchable region on the center side in the width direction while maintaining continuity by crossing the front around-leg elastic member and the back around-leg elastic member.

<Fifth Aspect>

In the trunks-type disposable diaper according to the fourth aspect, mutual intervals of the elastic members in a group of the front around-leg elastic members and mutual intervals of the elastic members in a group of the back around-leg elastic members are narrowed toward the center side in the width direction.

(Function and Effect)

In the present aspect, it is preferable that even if the cutting positions of the front around-leg elastic member and the back around-leg elastic member are somewhat shifted, or the cut elastic member is moved in the stretchable direction without being fixed, any one of the front around-leg elastic members and any one of the back around-leg elastic members cross each other, and the continuity of the front around-leg elastic members and the back around-leg elastic members tends to remain along the edge of the leg opening from the side seal portion of the front body to the side seal portion of the back body.

Advantageous Effects of Invention

As described above, according to the present invention, it is possible to prevent contraction in the width direction of the inner thigh contact portion and to prevent unpleasant wearing feeling and occurrence of a gap.

DESCRIPTION OF EMBODIMENTS

Figure 1:
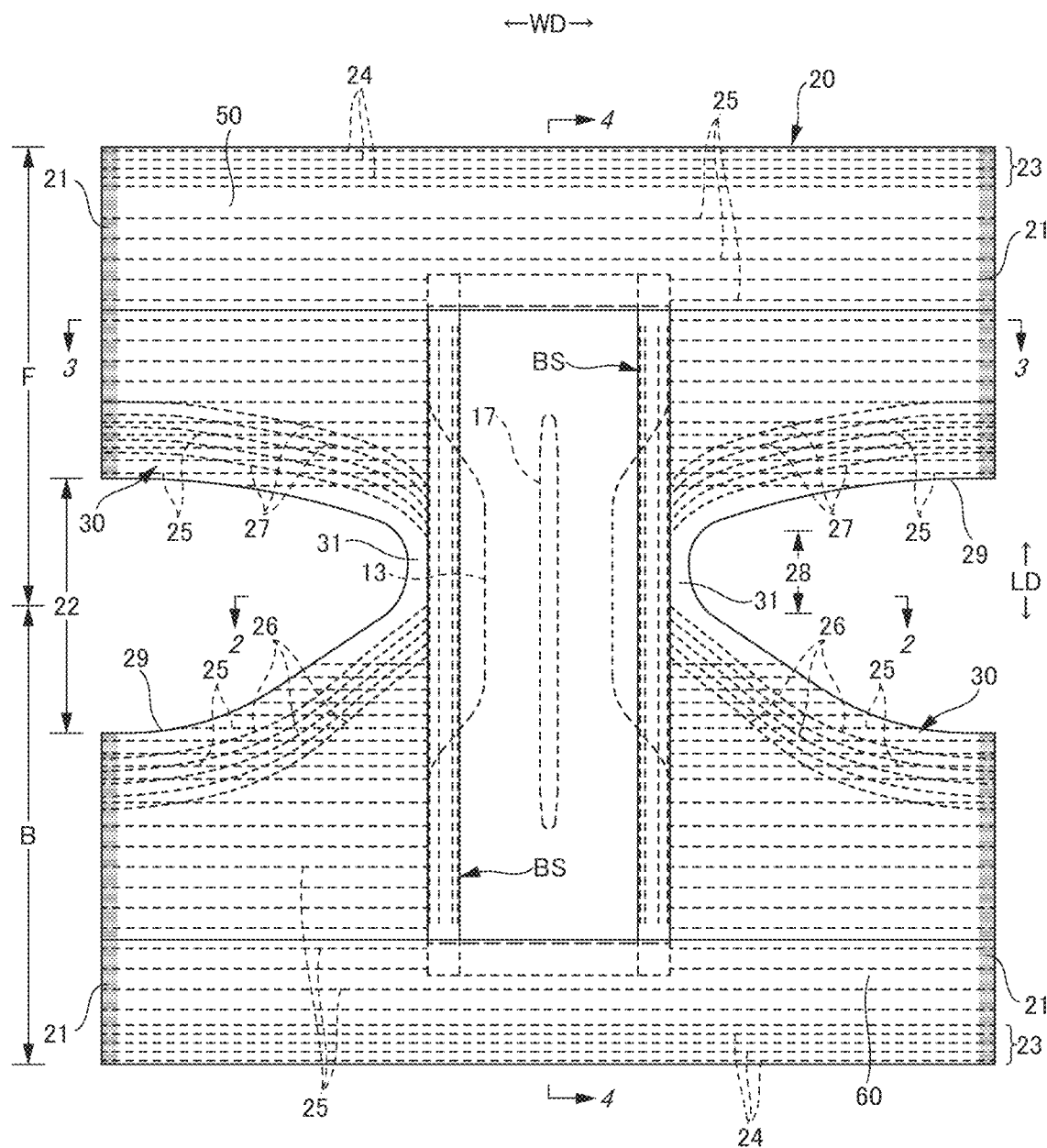
FIG. 1 is a plan view (internal surface side) of a trunks-type disposable diaper in a spread state.
Figure 2:
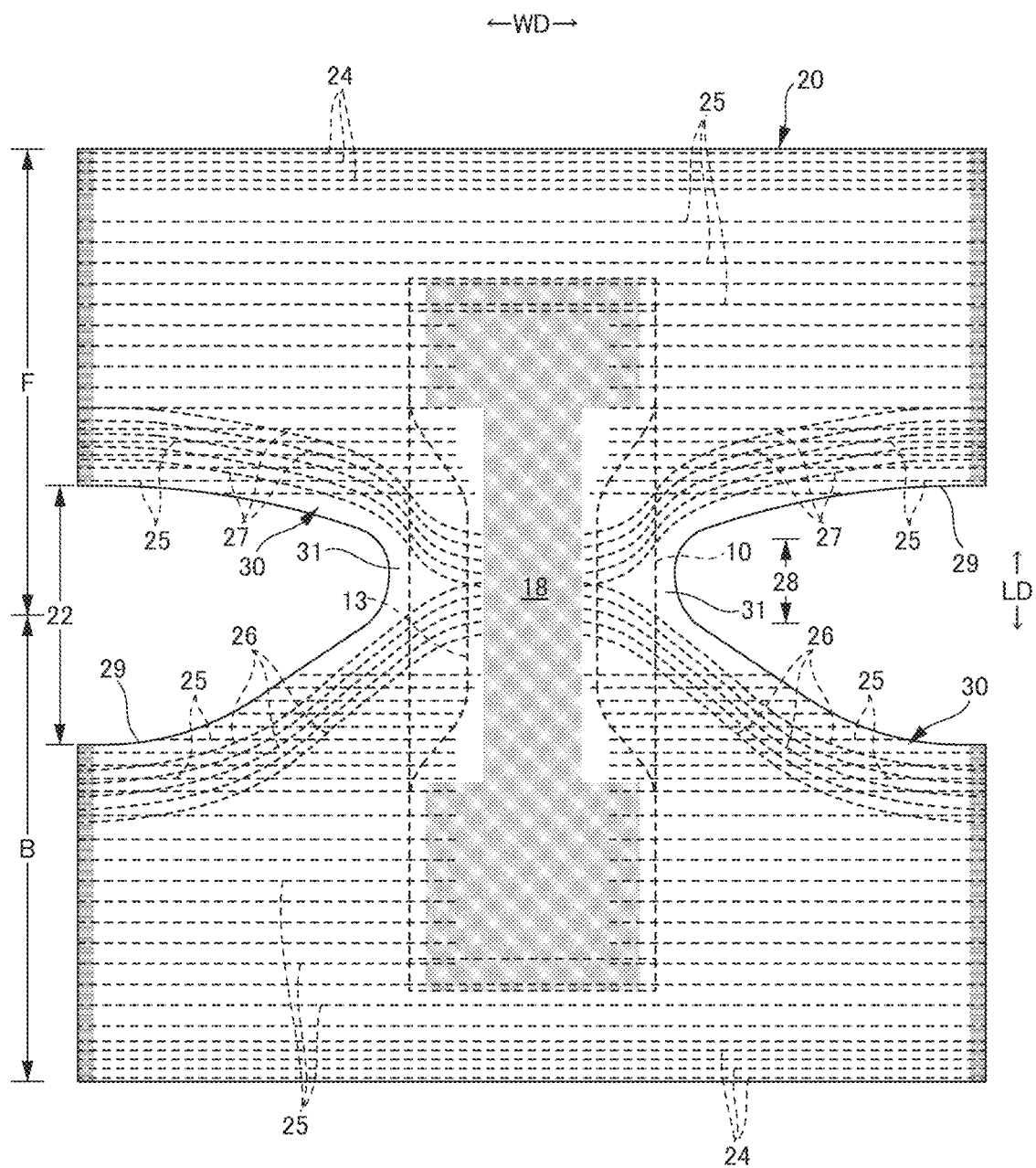
FIG. 2 is a plan view (external surface side) of a trunks-type disposable diaper in a spread state.
Figure 3:
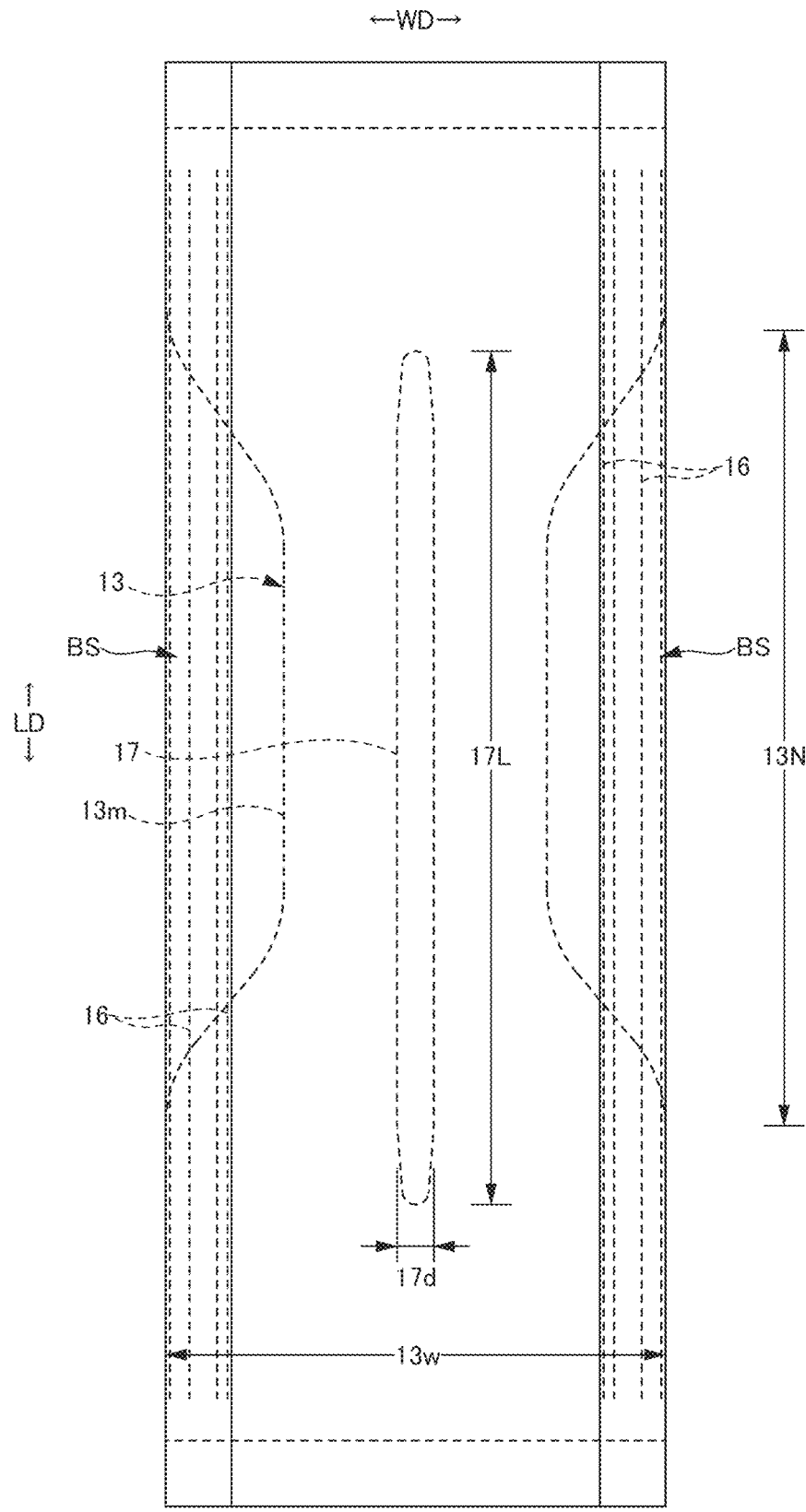
FIG. 3 is a plan view of an inner member.

Hereinafter, embodiments of the present invention will be described in detail with reference to the accompanying drawings. The term "stretch rate" means a value when the natural length is taken as 100%. In addition, dotted pattern portions in the drawings indicate a bonding means such as a hot melt adhesive.

FIGS. 1 to 10 illustrate a trunks-type disposable diaper. This trunks-type disposable diaper (hereinafter also simply referred to as a diaper) includes an outer member 20, an inner member 10, and side seal portions 21. The outer member 20 has a waist opening and a pair of leg openings and extends from an edge of a waist opening of a front body F to an edge of a waist opening of a back body B. The inner member 10 is provided at least in a crotch portion 28 of the outer member 20 and includes an absorber 13. The side seal portions 21 bond both sides on the front side and both sides on the back side of the outer member 20. The crotch portion 28 of the outer member 20 has a pair of inner thigh contact portions 31 respectively extending to one side and the other side in the width direction from the circumscribed rectangle of the absorber 13 (the circumscribed rectangle means a virtual rectangle circumscribing the absorber 13 in a plan view in a spread state. In this aspect, one opposite side of the circumscribed rectangle of the absorber 13 is substantially equal to both side edges of the inner member 10). Portions along the edges 29 of the leg openings including the inner thigh contact portions 31 are a pair of cylindrical leg portions 30 surrounding the root side of the thighs. Upon manufacturing, after the inner member 10 is bonded to the outer member 20 by a bonding means such as a hot melt adhesive, the inner member 10 and the outer member 20 are folded at the center in the front-back direction (longitudinal direction) which is a boundary between the front body F and the back body B, and both side portions thereof are bonded to each other by thermal welding, a hot melt adhesive, or the like to form the side seal portion 21. As a result, a trunks-type disposable diaper having a waist opening and a pair of leg openings can be formed.

(Structure Example of Inner Member)

As illustrated in FIGS. 3 to 6, the inner member 10 has a structure in which the absorber 13 is interposed between a liquid pervious top sheet 11 made of a nonwoven fabric and the liquid impervious sheet 12 made of polyethylene or the like to absorb and retain excreted fluid that has permeated through the top sheet 11. The planar shape of the inner member 10 is not particularly limited, but generally it is a substantially rectangular shape as the illustrated embodiment.

As the top sheet 11 covering a front surface side of the absorber 13 and forming a skin contact surface, a porous or nonporous nonwoven fabric, a porous plastic sheet, or the like is suitably used. For a raw material fiber forming a nonwoven fabric, in addition to synthetic fibers such as polyolefin type such as polyethylene or polypropylene, polyester type, polyamide type, etc., regenerated fibers such as rayon and cupra, and natural fibers such as cotton can be used, and a nonwoven fabric obtained by an appropriate processing method, such as a spun lace method, a spun bond method, a thermal bond method, a melt blown method, and a needle punch method can be used. In these processing methods, the spun lace method is excellent in terms of flexibility and drapability, and the thermal bond method is excellent in terms of bulkiness and softness. When a large number of through holes are formed on the top sheet 11, urine and the like are quickly absorbed, and dry touch property is excellent. In the illustrated form, the top sheet 11 is wound around the side edge portion of the absorber 13 and extends to the back surface side of the absorber 13, but is not limited thereto.

For the liquid impervious sheet 12 covering a back surface side of the absorber 13, a liquid impermeable plastic sheet such as polyethylene or polypropylene is used. In recent years, those having moisture permeability are preferably used from the viewpoint of prevention of stuffiness. Examples of this waterproof/moisture pervious sheet include a microporous sheet. The microporous sheet is obtained by stretching a sheet in one or two axial directions after forming the sheet by melt kneading an inorganic filler in a polyolefinic resin such as polyethylene and polypropylene.

As the liquid impervious sheet 12, it is desirable to use an opaque sheet such that brown color of excreta, urine, and the like does not appear. As the opaque sheet, a film obtained by internally adding a pigment or a filler such as calcium carbonate, titanium oxide, zinc oxide, white carbon, clay, talc, barium sulfate, or the like in a plastic is suitably used. In the illustrated embodiment, the liquid impervious sheet 12 is folded back to the back surface side together with the top sheet 11 on both sides in the width direction of the absorber 13, but is not limited thereto.

The absorber 13 is basically a known absorber, for example, laminates of pulp fibers, assembly of filaments such as cellulose acetate, or nonwoven fabrics, and as necessary, super absorbent polymers can be mixed therewith and fixed. The absorber 13 can be wrapped with a package sheet 14 having liquid permeability and liquid retention, such as crepe paper, as necessary, for shape and polymer retention and the like.

The entire shape of the absorber 13 is formed in a substantially hourglass shape having a narrower portion 13N narrower than both front and back sides thereof in the front-back direction range including the crotch portion 28. Although the size of the narrower portion 13N can be determined as appropriate, the length in the front-back direction of the narrower portion 13N can be set to about 20 to 50% of the maximum length of the diaper, and the width of the narrowest portion 13$m$ is about 40 to 60% of the maximum width of the absorber 13. In the case where such the narrower portion 13N is provided, if the planar shape of the inner member 10 is substantially rectangular, a remaining portion without the absorber 13 is formed at a portion corresponding to the narrower portion 13N of the absorber 13 in the inner member 10.

As illustrated in FIG. 1 and FIGS. 3 to 5, if the diffusion groove 17 extending in the front-back direction is provided in the intermediate portion in the width direction of the absorber 13, it is preferable since the diffusibility in the front-back direction of urine is improved. From the viewpoint of diffusibility of urine, it is preferable that the diffusion groove extends to both front and back sides of the intermediate region between the edge of one leg opening and the edge of the other leg opening. Only one diffusion groove 17 may be provided at the center in the width direction, but two diffusion grooves may be provided at an interval in the width direction. Although the diffusion groove 17 extends linearly in the illustrated embodiment, it may extend in a curved shape.

The diffusion groove 17 is preferably a slit penetrating the absorber 13 in the thickness direction as the illustrated embodiment, but it may be a concave portion provided on at least one side of the front and back of the absorber 13 and not penetrating it in the thickness direction. When the concave portion is formed in the absorber 13, the concave portion is formed by reducing the basis weight of the formation position of the concave portion in comparison with the surroundings, and also it can be formed by compressing the formation position of the concave portion by embossing.

The position of the diffusion groove forming region is not limited as long as it is provided at the intermediate portion in the width direction of the absorber 13, but normally, it is desirable that the diffusion groove forming region is located in the center in the width direction, and that the width thereof (the width of the diffusion groove 17$d$ in the case of one) is 5 to 20% of the maximum width 13$w$ of the absorber 13. Further, the length 17L in the front-back direction of the diffusion groove 17 can be determined as appropriate, and can be set to about 30 to 70% of the maximum length of the absorber 13, for example.

Figure 5:
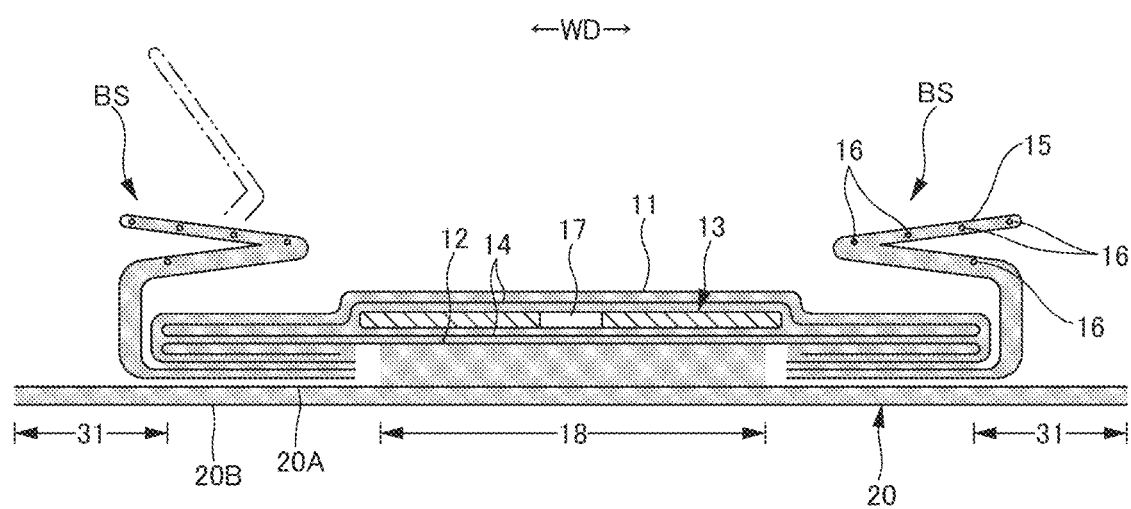
FIG. 5 is a cross-sectional view taken along line 2-2 in FIG. 1.
Figure 6:
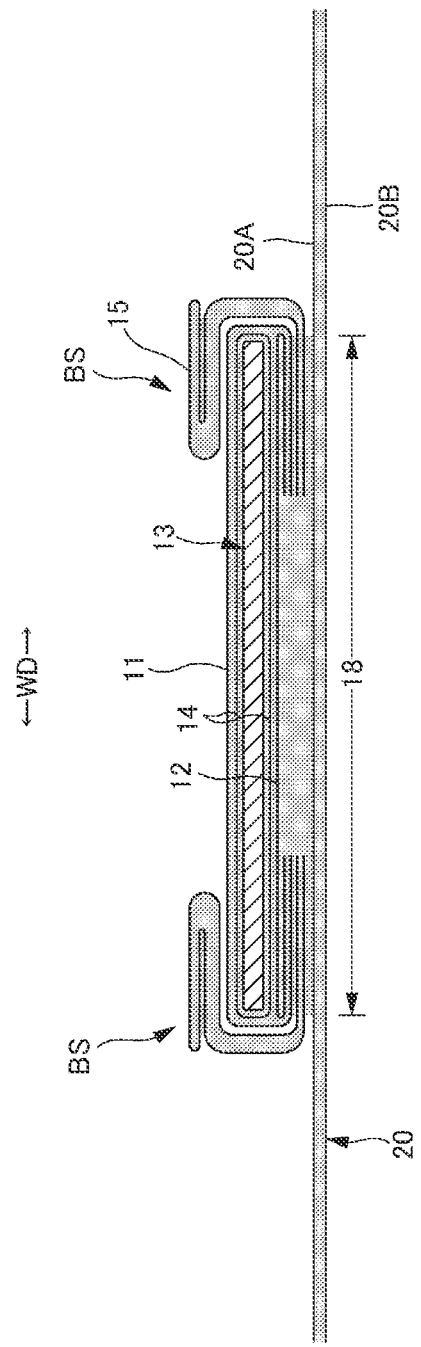
FIG. 6 is a cross-sectional view taken along line 3-3 in FIG. 1.
Figure 7:
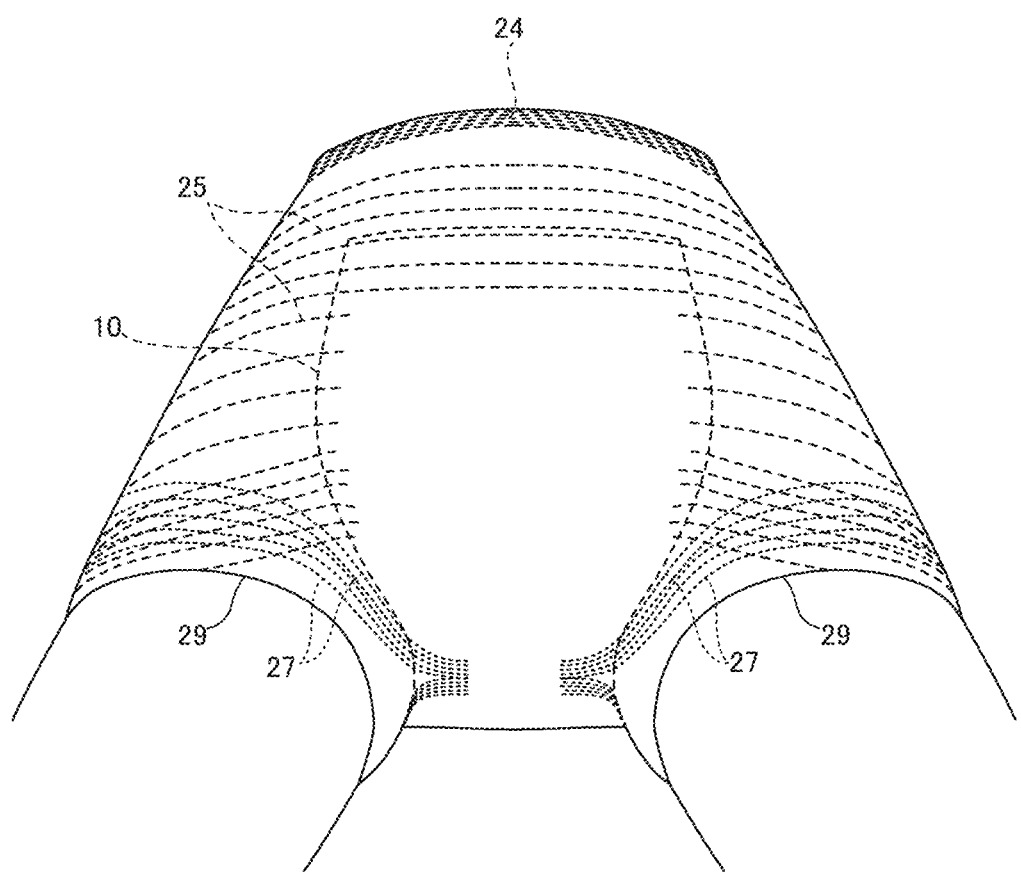
FIG. 7 is a perspective view as viewed obliquely from the lower front of a trunks-type disposable diaper in a wearing state.

Three-dimensional gathers BS fitting around the legs are formed on both sides of the inner member 10. As illustrated in FIGS. 5 and 6, the three-dimensional gather BS is formed of the double folded gather sheet 15 composed of a fixed portion, a main unit section, a fallen portion, and a free portion. The fixed portion is fixed to a side portion of a back surface of the inner member 10. The main unit section extends from the fixed portion through a side of the inner member 10 to a side portion of a front surface of the inner member 10. The fallen portion is formed by fixing the front and back end portions of the main unit section to the side portion of the surface of the inner member 10 in a fallen state. The free portion is formed by non-fixing between the fallen portions. A water-repellent nonwoven fabric is suitably used as the gather sheet 15.

Further, between the double gather sheets 15, an elongated gather elastic member 16 is disposed at a tip portion of the free portion or the like. As illustrated by a two-dot chain line in FIG. 5 in a product state, the gather elastic member 16 is used to form a three-dimensional gather BS by standing the free portion by an elastic stretching force.

As the gather elastic member 16, materials such as styrene rubber, polyolefin rubber, polyurethane rubber, polyester rubber, polyurethane, polyethylene, polystyrene, styrene butadiene, silicon, polyester, and the like which are usually used can be used. Further, in order to make it difficult to be seen from the outside, it is better that the thickness is set to 925 dtex or less, a stretch rate is set to 150 to 350%, and the interval is set to 10.0 mm or less. As the gather elastic member 16, in addition to a thread-like shape as the illustrated embodiment, a tape-shaped member having a certain width can be used.

A nonwoven fabric used for the gather sheet 15 is not particularly limited and can be made of, in addition to synthetic fibers such as polyolefin type such as polyethylene or polypropylene, polyester type, polyamide type, etc., regenerated fibers such as rayon and cupra, and natural fibers such as cotton. Further, the nonwoven fabric can be manufactured by an appropriate processing method, such as a spun bond method, a thermal bond method, a melt blown method, and a needle punch method. In particular, as the gather sheet 15, in order to prevent permeation of urine and the like, it is desirable to use a water-repellent treated nonwoven fabric coated with a silicone type, a paraffin metal type, an alkyl chromic chloride type water repellent agent or the like.

(Structure Example of Outer Member)

Figure 4:
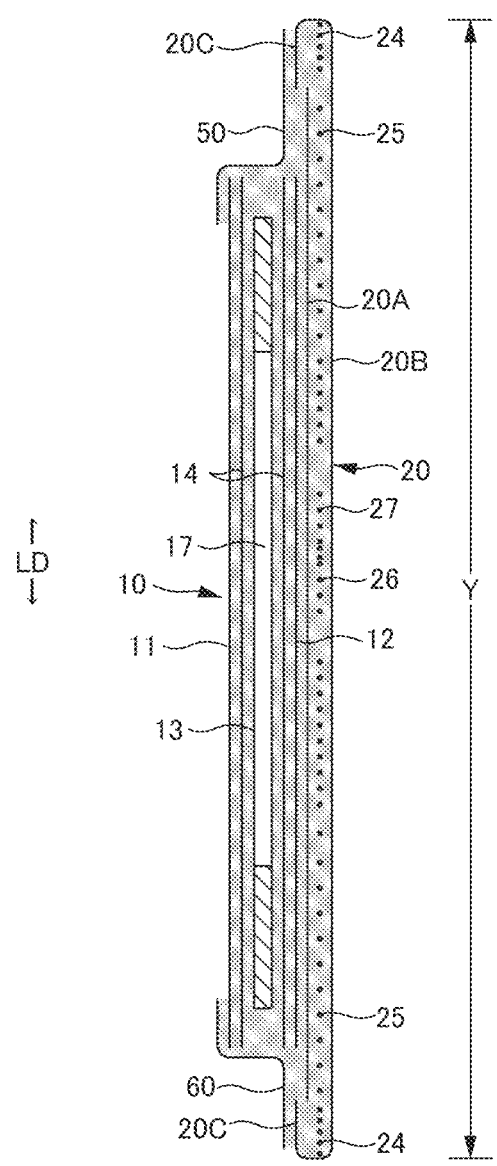
FIG. 4 is a cross-sectional view taken along line 4-4 in FIG. 1.

As also illustrated in FIG. 4, various elastic members 24 to 27 for imparting elasticity are provided on the outer member 20, a region having at least an elastic member (the entire region in the illustrated embodiment) has a plurality of sheet layers, and the elastic members 24 to 27 are sandwiched between these sheet layers. A plurality of the sheet layers can be formed by folding back one sheet material, in addition to each being formed by one sheet material. The outer member 20 in the illustrated embodiment has a two-layered structure including a pressing sheet 20A and a back sheet 20B each of which is made of a nonwoven fabric or the like, and the elasticity is imparted thereto by disposing various elastic members 24 to 27 between the pressing sheet 20A and the back sheet 20B and between the nonwoven fabrics of a folded-back portion 20C formed by folding the back sheet 20B toward the internal surface side at a waist opening edge.

Figure 14:
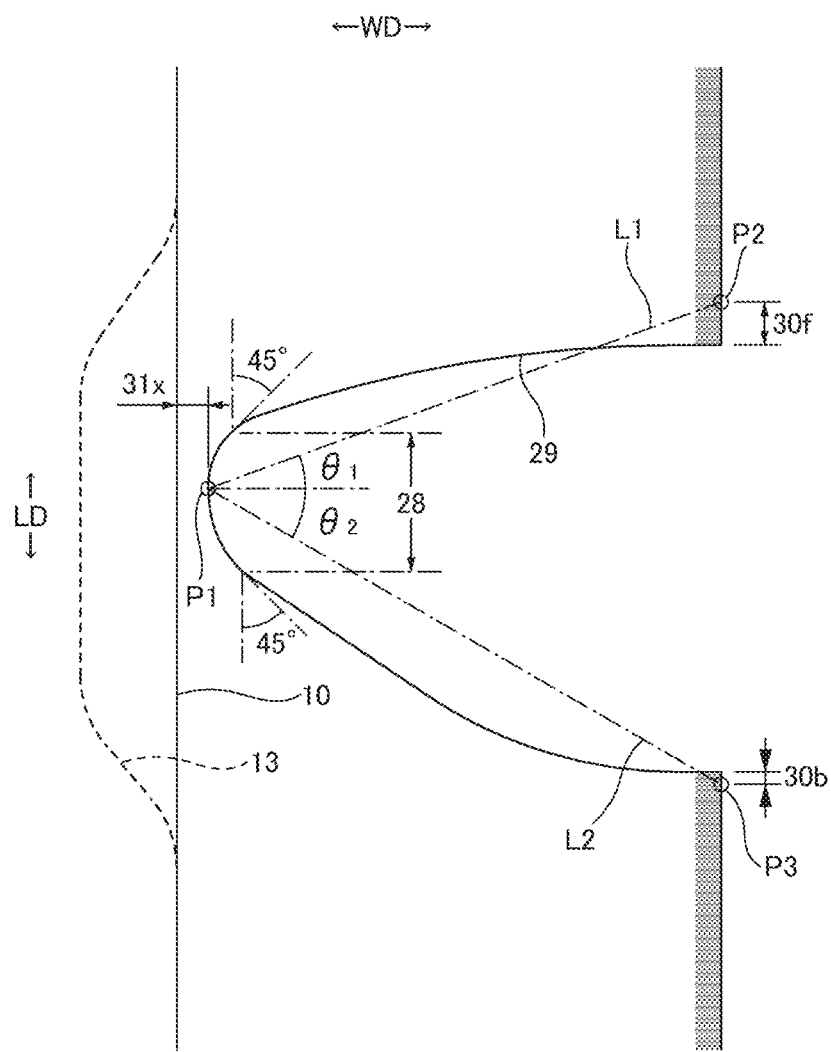
FIG. 14 is an enlarged plan view of a trunks-type disposable diaper in a spread state.

The outer member 20 has a substantially hourglass shape in which the middle in the front-back direction LD is narrow, and both side edges of the narrower portion are the edges 29 of the leg openings, respectively. As described above, the crotch portion 28 of the outer member 20 has a pair of inner thigh contact portions 31 respectively extending to one side and the other side in the width direction WD from the circumscribed rectangle of the absorber 13. The portions along the edges 29 of the leg openings including the inner thigh contact portions 31 form a pair of cylindrical leg portions 30 surrounding the root side of the thighs. The dimension of the inner thigh contact portion 31 may be appropriately determined according to the length of the cylindrical leg portion 30, but in the usual case, the width 31$x$ of the inner thigh contact portion 31 in the narrowest portion of the outer member 20 is preferably set to about 1 to 5% of the maximum length Y of the diaper. Further, as illustrated in FIG. 14, in the front body F, when a virtual straight line L1 is drawn which extends outward in the width direction and toward the waist side from a virtual point P1 positioned closest to the center side in the width direction on the edge 29 of the leg opening at an angle $\theta_1$ of 20 degrees with respect to the width direction, it is preferable to have a crossing point P2 between the virtual straight line L1 and the side edge of the outer member 20 in the front-back direction range having the side seal portion 21, and the front-back direction interval 30f from this crossing point P2 to the edge 29 of the leg opening is preferably equal to or larger than the width 31x of the inner thigh contact portion 31 in the narrowest portion of the outer member 20, and it is preferably substantially the same. On the other hand, in the back body B, when a virtual straight line L2 is drawn which extends outward in the width direction and toward the waist side from the virtual point P1 positioned closet to the center side in the width direction on the edge 29 of the leg opening at an angle $\theta_2$ of 30 degrees with respect to the width direction, it is preferable to have a crossing point P3 between the virtual straight line L2 and the side edge of the outer member 20 in the front-back direction range having the side seal portion 21, and the front-back direction interval 30b from this crossing point P3 to the edge 29 of the leg opening may be equal to or narrower than or equal to or wider than the width 31x of the inner thigh contact portion 31 in the narrowest portion of the outer member 20.

In the outer member 20 of the illustrated embodiment, each of the front body F and the back body B is provided with a waist elastic member 24, a lower waist portion elastic member 25, and a plurality of front around-leg elastic members 27 and back around-leg elastic members 26. The waist elastic member 24 is disposed along the width direction WD in the waist opening vicinity 23. The lower waist portion elastic member 25 is disposed along the width direction WD toward the leg opening side from the waist elastic member 24. The plurality of the front around-leg elastic members 27 and the back around-leg elastic members 26 is disposed at intervals without crossing each other in a curved pattern of extending from one of the side seal portions 21 along the edge 29 of the leg opening toward the center in the width direction WD, crossing the center in the width direction WD, extending toward the other leg opening, and extending to the other side seal portion 21 along the edge 29 of the other leg opening. Each of the elastic members 24 to 27 is fixed in a state of being elongated at a predetermined stretch rate along the extending direction thereof, so as to expand and contract together with the outer member 20 between the stretched state at the time of fixing and the natural length state. In the outer member 20, there is no around-leg elastic member continuous with one member from the side seal portion 21 of the front body F to the side seal portion 21 of the back body B along the edge 29 of the leg opening.

The waist elastic member 24 is an elongated elastic member such as a plurality of rubber threads disposed at intervals in the longitudinal direction at the waist opening vicinity 23 in the front-back direction range of the side seal portion 21 where the front body F and the back body B are bonded, and the waist elastic member 24 is for tightening and fitting the vicinity 23 of the waist opening of the diaper. Although a plurality of rubber threads are used as the waist elastic member 24 in the illustrated example, a tape-like stretchable member may be used, for example. Further, the waist elastic member 24 in the illustrated embodiment is sandwiched between the nonwoven fabrics of the folded-back portion 20C of the back sheet 20B in the waist portion, but it may be sandwiched between the pressing sheet 20A and the back sheet 20B.

The lower waist portion elastic member 25 is an elongated elastic member such as a plurality of rubber threads or the like disposed at intervals in the longitudinal direction in the region on the leg opening side of the waist elastic member 24 in the range in the front-back direction having the side seal portion 21. The lower waist portion elastic member is for tightening and fitting substantially the whole of a lower torso of the diaper except for the vicinity 23 of the waist opening. Now that, the boundary between the waist elastic member 24 and the lower waist portion elastic member 25 is positioned at a position where the stretching characteristic changes, such as the thickness and stretch rate of the elastic member, or the boundary is positioned at the waist side edge of the inner member 10 when the stretching characteristics do not change. It is desirable that the lower waist portion elastic member 25 be not provided in the crotch portion 28 as the illustrated embodiment. Further, on both front and back sides of the intermediate region 22, the lower waist portion elastic member 25 may be provided as illustrated embodiment, but it may not be provided.

In the outer member 20 of the back body B, the back around-leg elastic member 26 disposed separately from the lower waist portion elastic member 25 is an elongated elastic member such as a rubber thread, and at least one elastic member, preferably a plurality of elastic members, is disposed along a predetermined curve passing through the cylindrical leg portion 30 of the back body B. Although one back around-leg elastic member 26 may be provided, it is preferable that a plurality of elastic members are provided. In the illustrated example, an elongated elastic members such as five rubber threads is provided, and the back around-leg elastic members 26 do not cross each other but are disposed at intervals therebetween. A group of the back around-leg elastic members 26 is not disposed in a substantially bundle with the elastic members being closely spaced, and three or more, preferably four or more, elastic members are disposed at intervals of about 3 to 20 mm, preferably about 6 to 16 mm so as to form a predetermined stretching zone including the cylindrical leg portion 30 of the back body B.

In the outer member 20 of the front body F, the front around-leg elastic member 27 disposed separately from the lower waist portion elastic member 25 is an elongated elastic member such as a rubber thread, and at least one elastic member, preferably a plurality of elastic members, is disposed along a predetermined curve passing through the cylindrical leg portion 30 of the front body F. Although one front around-leg elastic member 27 may be provided, it is preferable that a plurality of elastic members is provided. In the illustrated example, elongated elastic members such as five rubber threads are provided, and the front around-leg elastic members 27 do not cross each other but are disposed at intervals therebetween. A group of the front around-leg elastic members 27 is not disposed in a substantially bundle with the elastic members being closely spaced, and three or more, preferably four or more, elastic members are disposed at intervals of about 3 to 20 mm, preferably about 6 to 16 mm so as to form a predetermined stretching zone including the cylindrical leg portion 30 of the front body F. The number of the front around-leg elastic members 27 is preferably equal to the number of the back around-leg elastic members 26, but it is also possible to set them to different numbers as necessary.

The front around-leg elastic member 27 and the back around-leg elastic member 26 need not be entirely curved, and may have a partially linear portion.

As a method for attaching the front around-leg elastic member 27 and the back around-leg elastic member 26, for example, the techniques described in JP 4-28363 A and JP 11-332913 A can be adopted.

Figure 10:
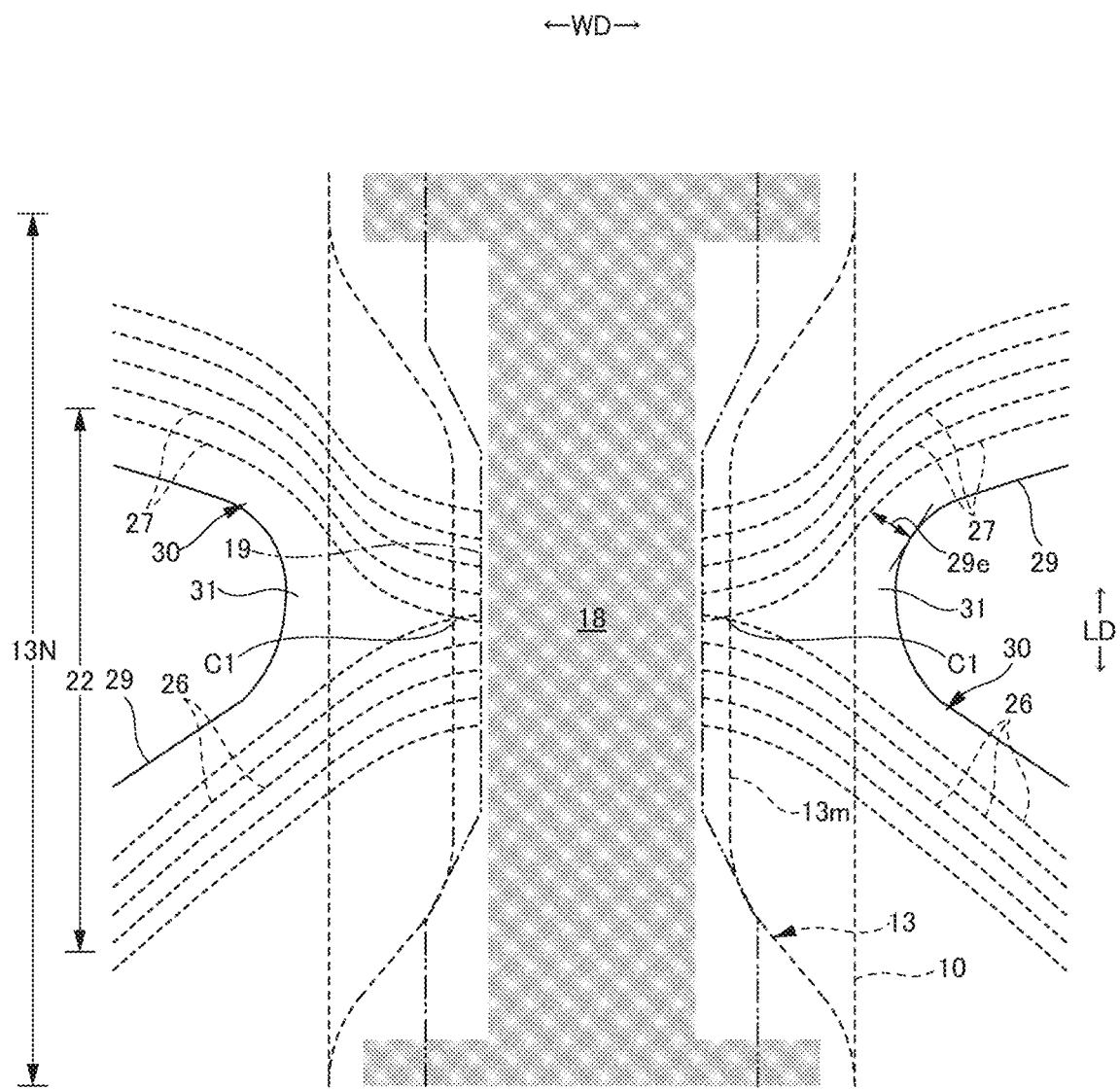
FIG. 10 is an enlarged plan view of a main part of FIG. 2.
Figure 12:
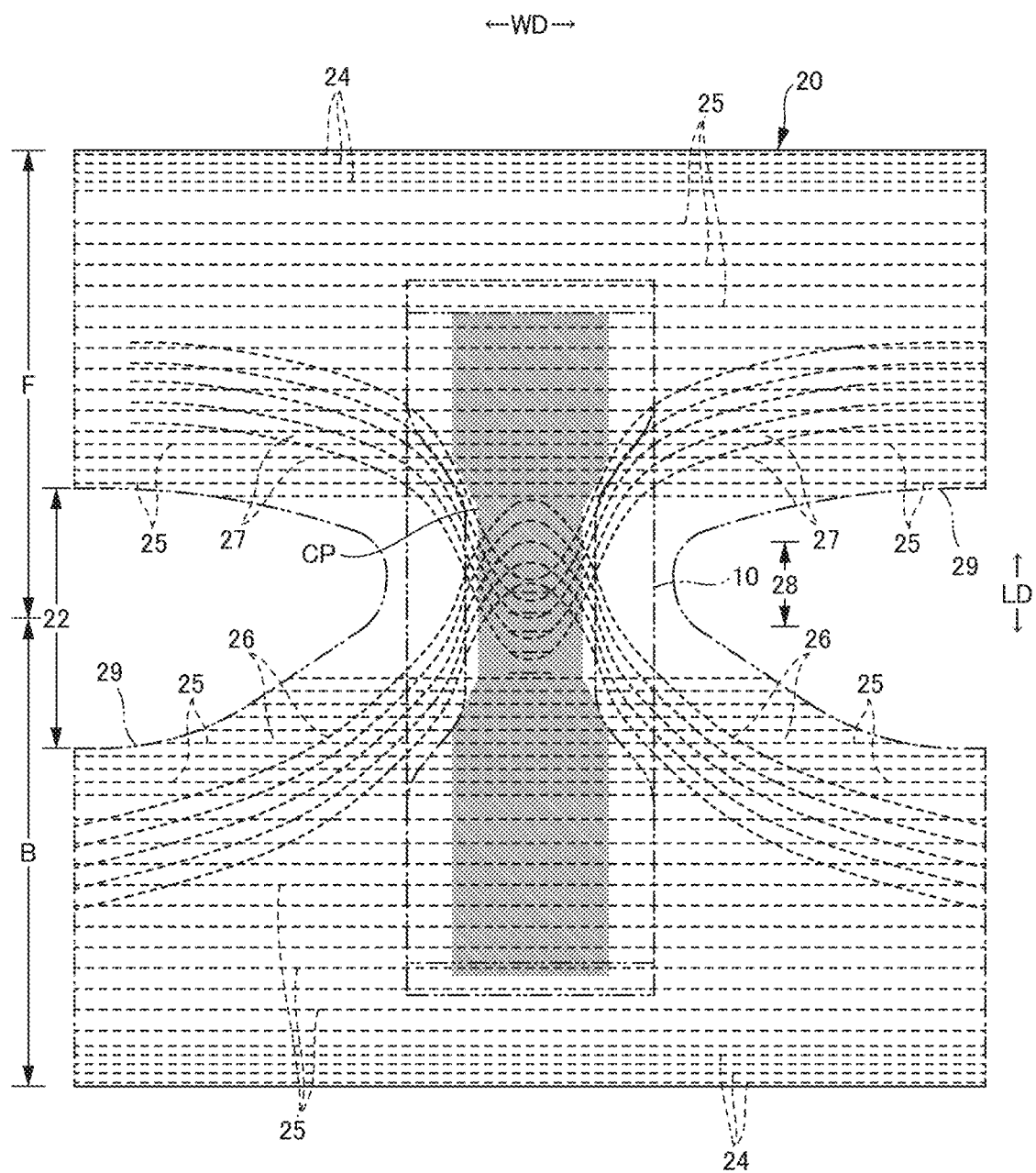
FIG. 12 is a plan view illustrating another pattern of a leg around-elastic member.

As illustrated in FIG. 10, the front around-leg elastic member 27 and the back around-leg elastic member 26 are attached in a pattern in which at least one of the front around-leg elastic members 27 and at least one of the back around-leg elastic members 26 cross each other on both sides in the width direction of the intermediate region 22 between the edge 29 of one leg opening and the edge 29 of the other leg opening. As a result, the front around-leg elastic member 27 and the back around-leg elastic member 26 cross each other and are substantially continuous along the leg opening, and the elasticity is imparted over the entire circumferential direction of the cylindrical leg portion 30. The number of crossing members of the front around-leg elastic members 27 and the back around-leg elastic members 26 may be one each at the front and back as in the form illustrated in FIG. 2, and also all the front around-leg elastic members 27 and the back around-leg elastic members 26 may cross as in the embodiment illustrated in FIGS. 12 and 13.

Characteristically, a crossing position C1 of the front around-leg elastic member 27 and the back around-leg elastic member 26 positioned closest to the edge 29 side of the leg opening is positioned at the same position in the width direction WD as the side edge of the narrowest portion 13m of the narrower portion 13N or at the center side in the width direction WD, and the crotch portion 28 does not have elastic members other than the front around-leg elastic member 27 and the back around-leg elastic member 26. This makes it difficult for the contraction forces of the front around-leg elastic member 27 and the back around-leg elastic member 26 to attract the inner thigh contact portion 31 to the center side in the width direction WD, and it is possible to suppress shortening of the length of the inner thigh contact portion 31, thereby making it possible to prevent deterioration of the wearing feeling and occurrence of a gap.

In particular, when the interval between the edge 29 of the leg opening and the elastic member closest to the edge 29 of the leg opening is narrow, the crossing position C1 of the front around-leg elastic member 27 and the back around-leg elastic member 26 is likely to be close to the edge 29 of the leg opening. Therefore, it is difficult to position the crossing position further to the center side in the width direction WD than the side edge of the narrowest portion of the narrower portion 13N in the absorber 13. Therefore, in the front around-leg elastic member 27 and the back around-leg elastic member 26, the interval 29e between the edge 29 of the leg opening and the elastic member closest to the edge 29 of the leg opening in the direction orthogonal to the tangent of the edge 29 of the leg opening is preferably 10 mm or more, and particularly preferably 10 to 50 mm in the crotch portion 28.

Figure 8:
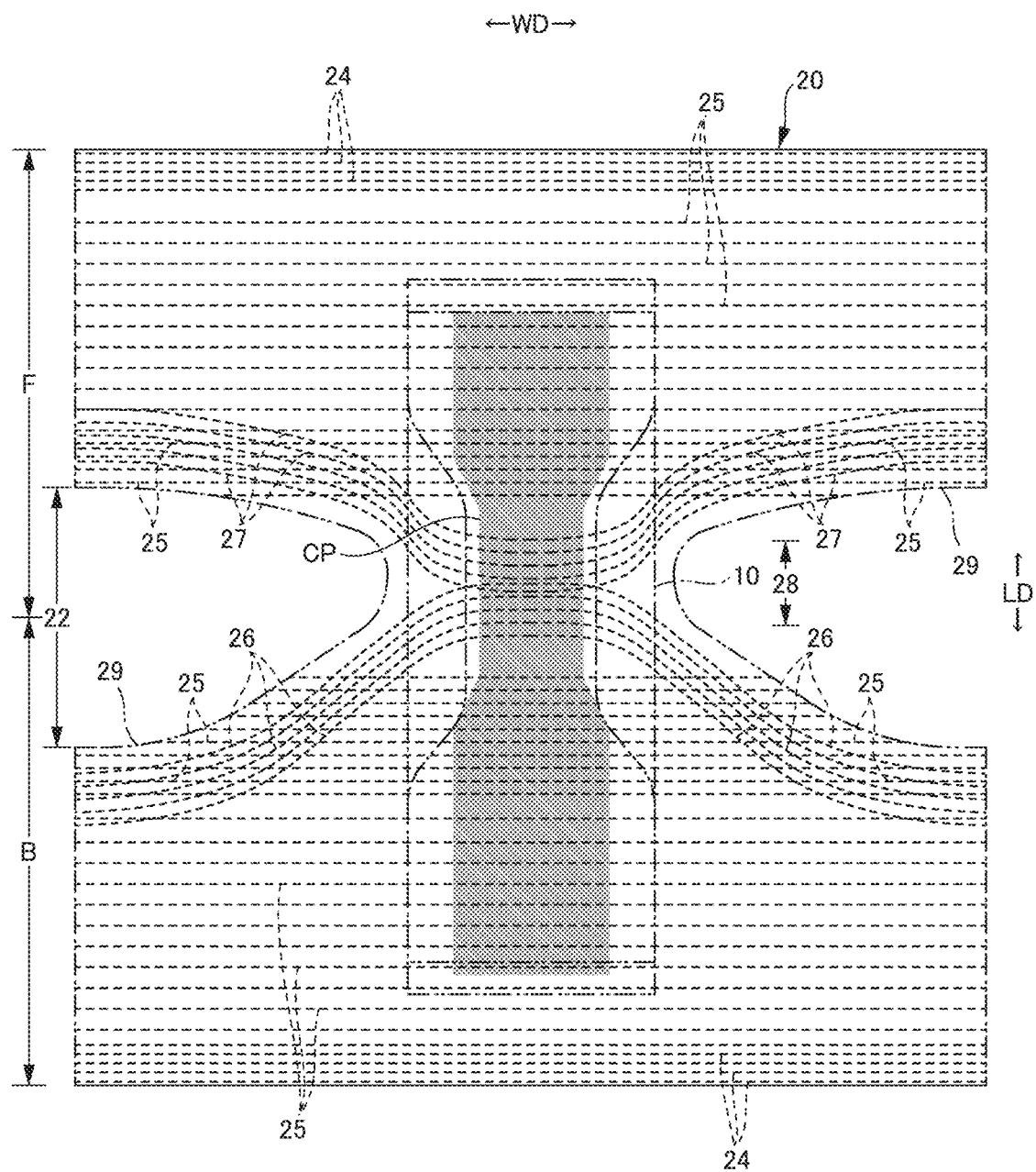
FIG. 8 is a plan view illustrating a cut pattern of an elastic member.

As illustrated in FIG. 8, the lower waist portion elastic member 25, the front around-leg elastic member 27, and the back around-leg elastic member 26 are continuously fixed to the outer member 20 at the time of manufacturing, and then, a part or all of the portion overlapping with the inner member bonded portion 18 is finely cut according to the predetermined cutting pattern CP to become the non-stretchable region 19 which does not expand and contract (that is, a portion overlapping with the cutting pattern CP in FIG. 8). A portion extending laterally from the non-stretchable region 19 may be a stretchable region (that is, the portion in which the lower waist portion elastic member 25, the front around-leg elastic member 27, and the back around-leg elastic member 26, positioned on the side of the cutting pattern CP in FIG. 8, is continuously left). In this case, the lower waist portion elastic member 25, the front around-leg elastic member 27, and the back around-leg elastic member 26 are continuously provided from the side seal portion 21 on one side to the side seal portion 21 on the other (opposite) side across the inner member 10, and then a part or all of the portion overlapping with the inner member bonded portion 18 is cut finely. Thereby, it is possible to prevent unnecessary shrinkage in the width direction of the inner member 10 (in particular, the absorber 13).

Figure 15:
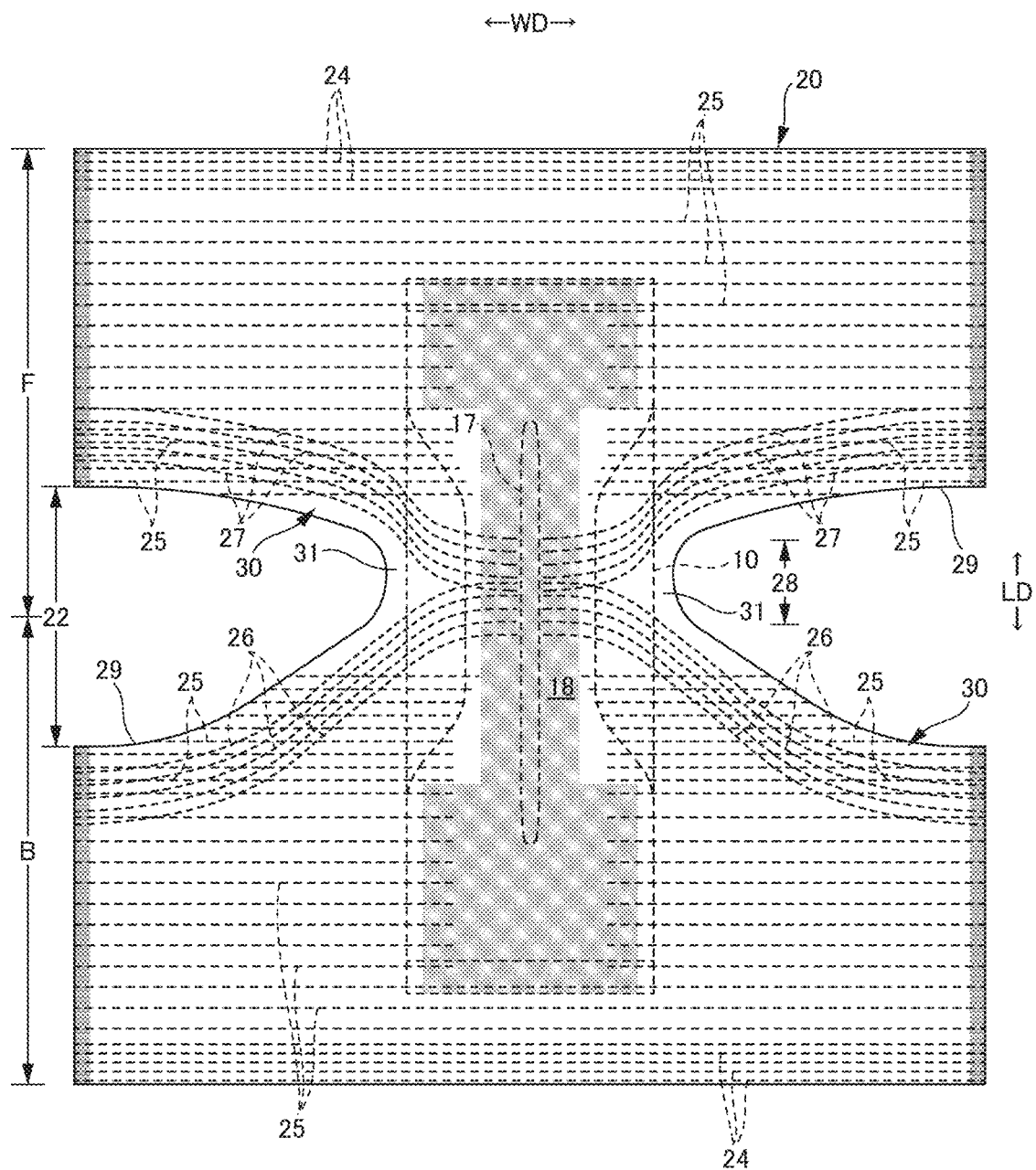
FIG. 15 is a plan view (external surface side) of a trunks-type disposable diaper in a spread state.
Figure 16:
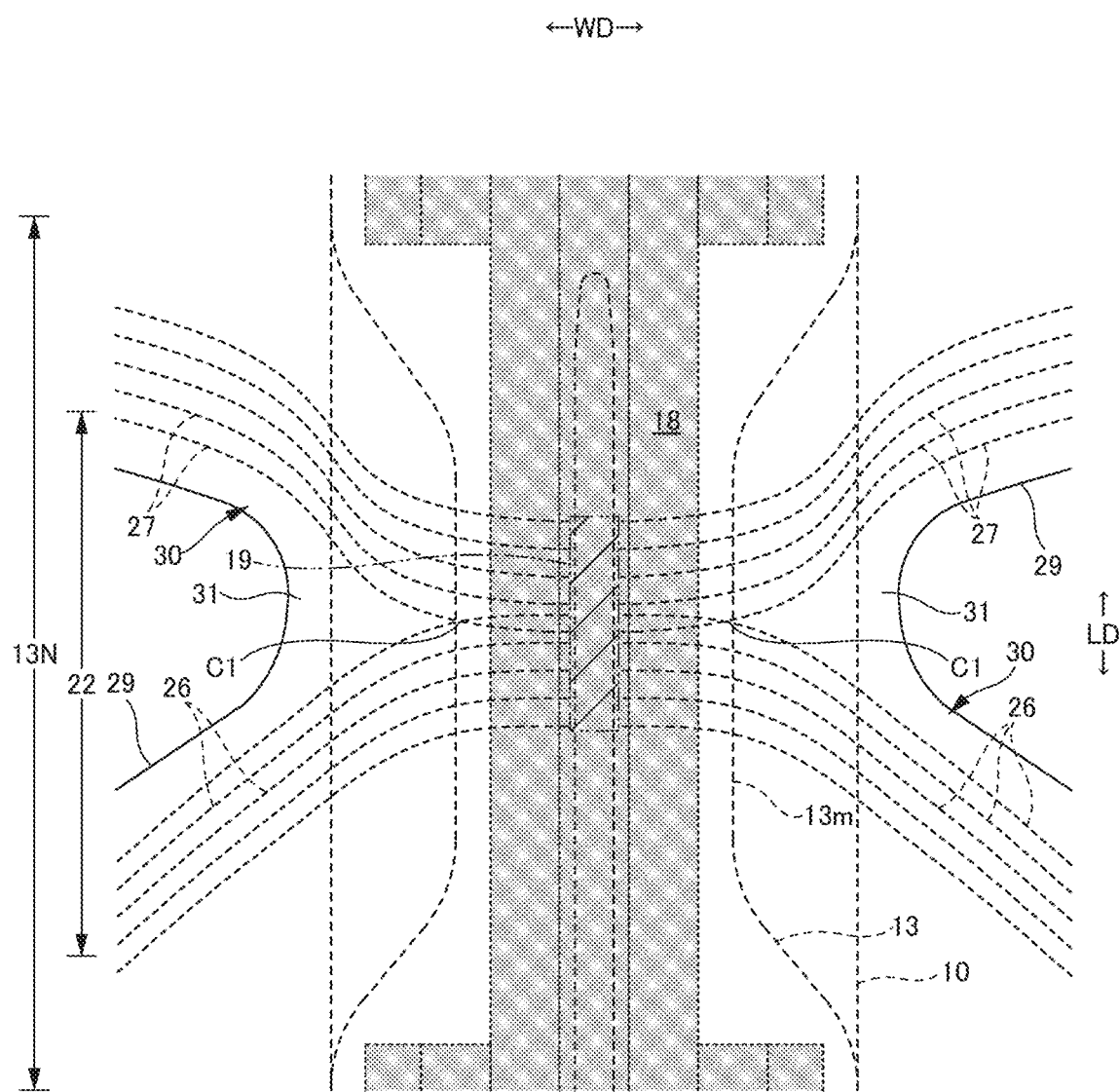
FIG. 16 is an enlarged plan view of a main part of FIG. 15.

In the case where the absorber 13 has the diffusion groove 17, as illustrated in FIGS. 15 and 16, it is preferable that at least one of the front around-leg elastic member 27 and the back around-leg elastic member 26 extends from the side seal portions 21 on both sides in the width direction WD to a portion at least overlapping with the side portion of the absorber 13 and is cut at a portion overlapping with the diffusion groove 17, and a portion overlapping with the diffusion groove 17 in the outer member 20 is a non-stretchable region 19. In particular, as the illustrated embodiment, at least one of the front around-leg elastic member 27 and the back around-leg elastic member 26 extends to the end on the diffusion groove 17 side in the region between the side edge of the absorber 13 and the diffusion groove 17 and is cut at a portion overlapping with the diffusion groove 17, and a portion overlapping with the diffusion groove 17 in the outer member 20 is the non-stretchable region 19. At the time of wearing, in the crotch portion 28, the absorber 13 is sandwiched between the legs, and the width is reduced, but at least one of the front around-leg elastic member 27 and the back around-leg elastic member 26 extends to the side portion of the absorber 13 and is cut at a portion overlapping with the diffusion groove 17. Consequently, the contraction force of the elastic member acts to spread the diffusion groove 17 on both sides in the width direction, and collapse of the diffusion groove 17 is prevented. In particular, in the case of the front around-leg elastic member 27 and the back around-leg elastic member 26 in the trunks-type disposable diaper as the illustrated embodiment, the angle between the contraction direction and the width direction WD becomes small, the component in the width direction of the contraction force becomes large, and the collapse of the diffusion groove 17 can be more effectively prevented.

Although it is conceivable to use other elastic members, for example, the waist elastic member 24 and the lower waist portion elastic member 25, since the elastic members 24 and 25 in the lower torso region corresponding to the side seal portion 21 do not pass through the intermediate region 22, the collapse of the diffusion groove 17 cannot be prevented in the intermediate region 22 which is a portion sandwiched between the legs. Further, although the lower waist portion elastic member 25 may be provided in the intermediate region 22, since one end of the lower waist portion elastic member 25 is positioned at the leg opening instead of the side seal portion 21, the collapse of the diffusion groove 17 cannot be suppressed even if the lower waist portion elastic member 25 is used.

In the case where the collapse of the diffusion groove 17 is prevented by the front around-leg elastic member 27 and the back around-leg elastic member 26, although not illustrated, when the front around-leg elastic member 27 and the back around-leg elastic member 26 are provided in a front-back symmetrical arrangement with respect to the number and arrangement thereof, the longitudinal component of the contraction force of the front around-leg elastic member 27 and the back around-leg elastic member 26 is canceled out each other, and the force in the width direction WD acts well in balance with respect to both sides of the diffusion groove 17 in the absorber 13, and the effect of preventing the diffusion groove 17 from being collapsed is further enhanced.

Figure 13:
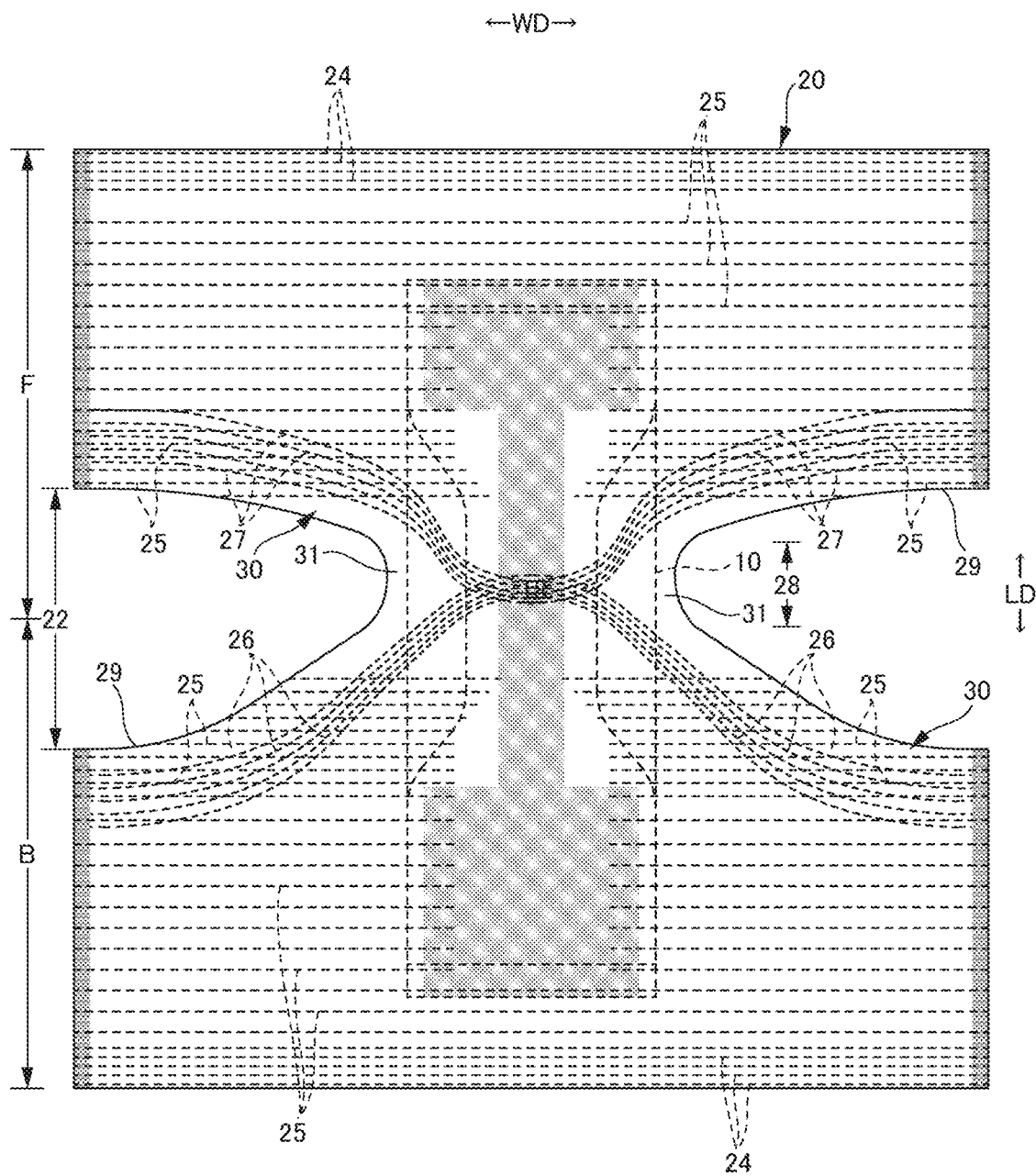
FIG. 13 is a plan view (external surface side) of a trunks-type disposable diaper in a spread state.

In the case where at least one of the front around-leg elastic members 27 and at least one of the back around-leg elastic members 26 cross each other on both sides in the width direction of the intermediate region 22, the front around-leg elastic member 27 and the back around-leg elastic member 26 are cut on the center side in the width direction from the crossing position. In the case where a group of a plurality of the front around-leg elastic members 27 and a group of a plurality of the back around-leg elastic members 26 cross on both sides in the width direction WD of the intermediate region 22, as illustrated in FIG. 13, if a mutual interval of the elastic members in the group of the front around-leg elastic members 27 and a mutual interval between the elastic members in the group of the back around-leg elastic members 26 are narrowed toward the center in the width direction, it is preferable that even if the cutting positions are somewhat shifted, or the cut elastic member is moved in the stretchable direction without being fixed, any one of the front around-leg elastic members 27 and any one of the back around-leg elastic members 26 cross each other, and the continuity of the front around-leg elastic members 27 and the back around-leg elastic members 26 tends to remain along the edge 29 of the leg opening from the side seal portion 21 of the front body F to the side seal portion 21 of the back body B.

As a method of cutting the elastic members 24 to 27 to form the non-stretchable region, for example, the techniques described in JP 2002-35029 A, JP 2002-178428 A, and JP 2002-273808 A can be adopted. It is obvious that the lower waist portion elastic member 25, the front around-leg elastic member 27, and the back around-leg elastic member 26 can also be disposed continuously across the inner member 10 without being cut.

Although the stretch rate at the time of fixing the elastic members 24 to 27 can be appropriately determined, for normal adult use, about 160 to 320% for the waist elastic member 24, about 160 to 320% for the lower waist portion elastic member 25, and about 230 to 350% for the front around-leg elastic member 27 and the back around-leg elastic member 26. In particular, in the case where a plurality of the front around-leg elastic members 27 and the back around-leg elastic members 26 are provided, with increasing proximity to the edge of the leg opening, the stretch rate is gradually increased, and conversely the stretch rate is gradually decreased, in one preferred embodiment. Instead of or in conjunction with this change in the stretch rate, the thickness of the elastic member can be varied as well.

Figure 9:
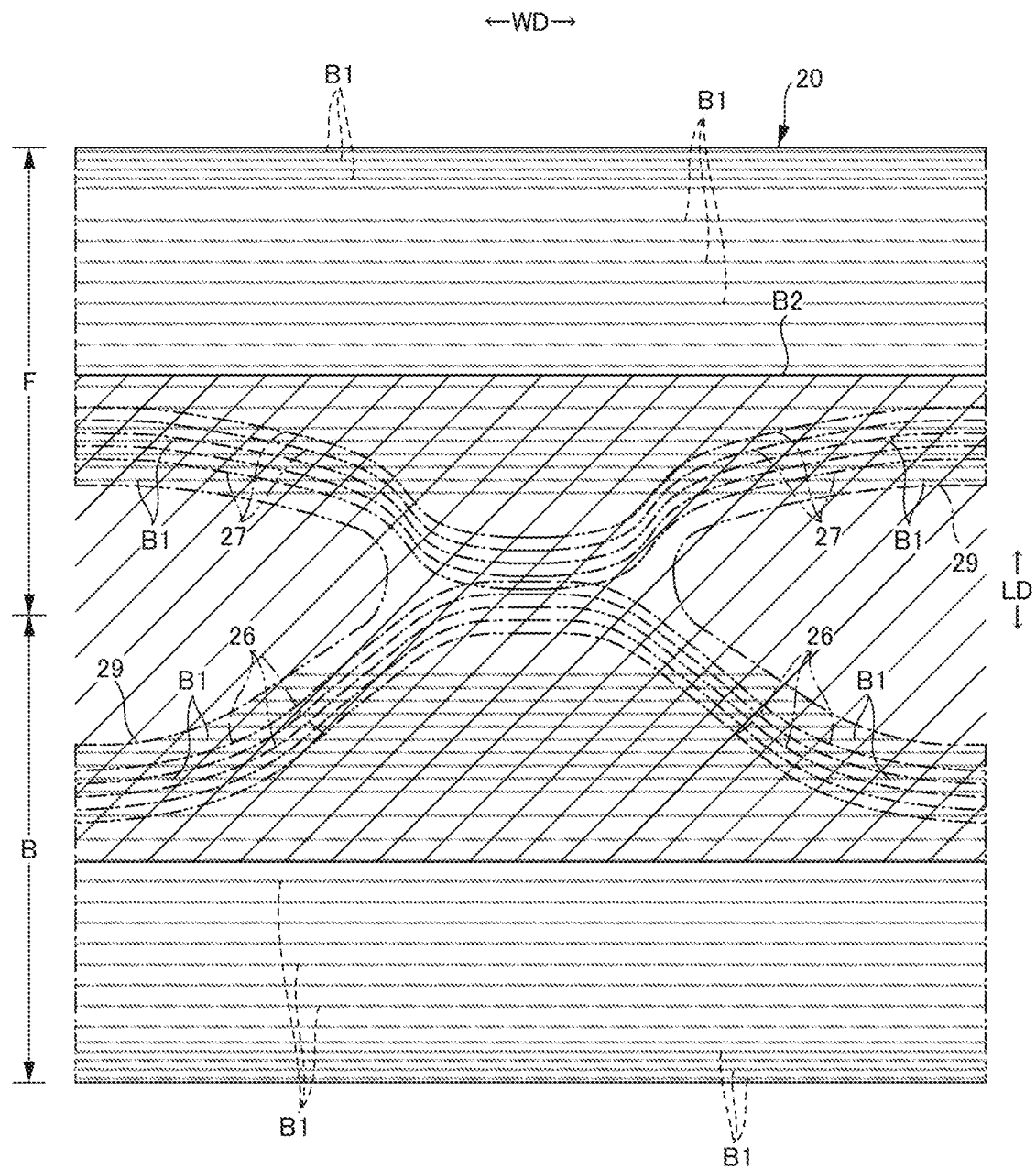
FIG. 9 is a plan view illustrating an adhesive application pattern.

The waist elastic member 24, the lower waist portion elastic member 25, and the around-leg elastic members 26, 27 are sandwiched between the folded-back portions 20C of the back sheet and between the pressing sheet 20A and the back sheet 20B, and those are adhered and fixed to the sheets 20A and 20B by a hot melt adhesive. The application pattern of the hot melt adhesive can be determined as appropriate, but as illustrated in FIG. 9, it is preferable that the adhesive portion (hot melt adhesive B1) for fixing the waist elastic member 24 and the lower waist portion elastic member 25 is only the arrangement portion and the vicinity of the waist elastic member 24, the arrangement portion and the vicinity of the lower waist portion elastic member 25. FIG. 9 illustrates the application site of the hot melt adhesive B1 in the manufacturing process, and the hot melt adhesive B1 for fixing the waist elastic member 24 and the lower waist portion elastic member 25 to both the sheets 20A and 20B is substantially applied only to the place where the elastic members 24 and 25 are disposed and the vicinity thereof. Such application of the adhesive can be realized by sandwiching the waist elastic member 24 with the adhesive applied on the outer peripheral surface and the lower waist portion elastic member 25 between both sheets 20A and 20B.

On the other hand, as illustrated in FIG. 9, the hot melt adhesive B2 for fixing the around-leg elastic members 26 and 27 to the pressing sheet 20A and the back sheet 20B is continuously applied in the width direction over the entire range in the front-back direction having the around-leg elastic members 26 and 27 and also can be applied in a stepwise manner along the around-leg elastic members 26 and 27 (not illustrated).

(Front and Back Pressing Sheet)

As also illustrated in FIGS. 1 and 4, in order to cover the front and back end portions of the inner member 10 attached on the inner surface of the outer member 20 and prevent leakage from the front and back edges of the inner member 10, the front and back pressing sheets 50, 60 may be provided. To describe the illustrated embodiment in more detail, the front pressing sheet 50 extends in the entire width direction from the inner surface of the folded-back portion 20C of the inner surface of the front body F to a position overlapping the front end portion of the inner member 10, and the back pressing sheet 60 extends from the inner surface of the folded-back portion 20C of the inner surface of the back body B to the position overlapping with the back end portion of the inner member 10 in the entire width direction. As the illustrated embodiment, when the front and back pressing sheets 50 and 60 are attached as separate bodies, although there is an advantage that the degree of freedom of material selection increases, there are a disadvantage such as an increase in materials and manufacturing processes. Therefore, it is also possible to form a portion equivalent to the above-described pressing sheets 50, 60 by extending the folded-back portion 20C to a portion overlapping with the inner member 10.

(Inner Member Bonded Portion)

As illustrated in the enlarged view of FIG. 10, it is preferable that the inner member bonded portion 18 which is a bonded region of the outer member 20 and the inner member 10 is provided only further to the center side in the width direction WD than the crossing position C1 of the front around-leg elastic member 27 and the back around-leg elastic member 26 on both sides in the width direction WD in the intermediate region 22. As a result, since the front around-leg elastic member 27 and the back around-leg elastic member 26 do not extend and contract with the inner member 10 in the intermediate region 22, the fitting is not deteriorated at a portion including the crossing position C1 between the front around-leg elastic member 27 and the back around-leg elastic member 26 though the front around-leg elastic member 27 and the back around-leg elastic member 26 cross each other and are substantially continuous along the edge 29 of the leg opening.

The inner member bonded portion 18 may be positioned only further to the center side in the width direction WD than the crossing position C1 of the front around-leg elastic member 27 and the back around-leg elastic member 26 on both sides in the width direction WD over the entire front-back direction. However, it is preferable that the inner member bonded portion 18 extends to the outside in the width direction WD from the crossing position C1 on both front and back sides of the intermediate region 22 as the illustrated embodiment.

When the stretchable region of the front around-leg elastic member 27 and the back around-leg elastic member 26 is provided to the center side in the width direction WD from the crossing position C1 of the front around-leg elastic member 27 and the back around-leg elastic member 26 on both sides in the width direction WD, the wearing feeling is deteriorated due to the contraction of the absorber 13 in the width direction WD. Accordingly, as the illustrated embodiment, it is preferable that, while maintaining the continuity by crossing the front around-leg elastic member 27 and the back around-leg elastic member 26, the non-stretchable region 19 in which the front around-leg elastic member 27 and the back around-leg elastic member 26 are cut finely is provided further to the center side in the width direction WD than the crossing position C1 of the front around-leg elastic member 27 and the back around-leg elastic member 26 on both sides in the width direction WD.

Figure 11:
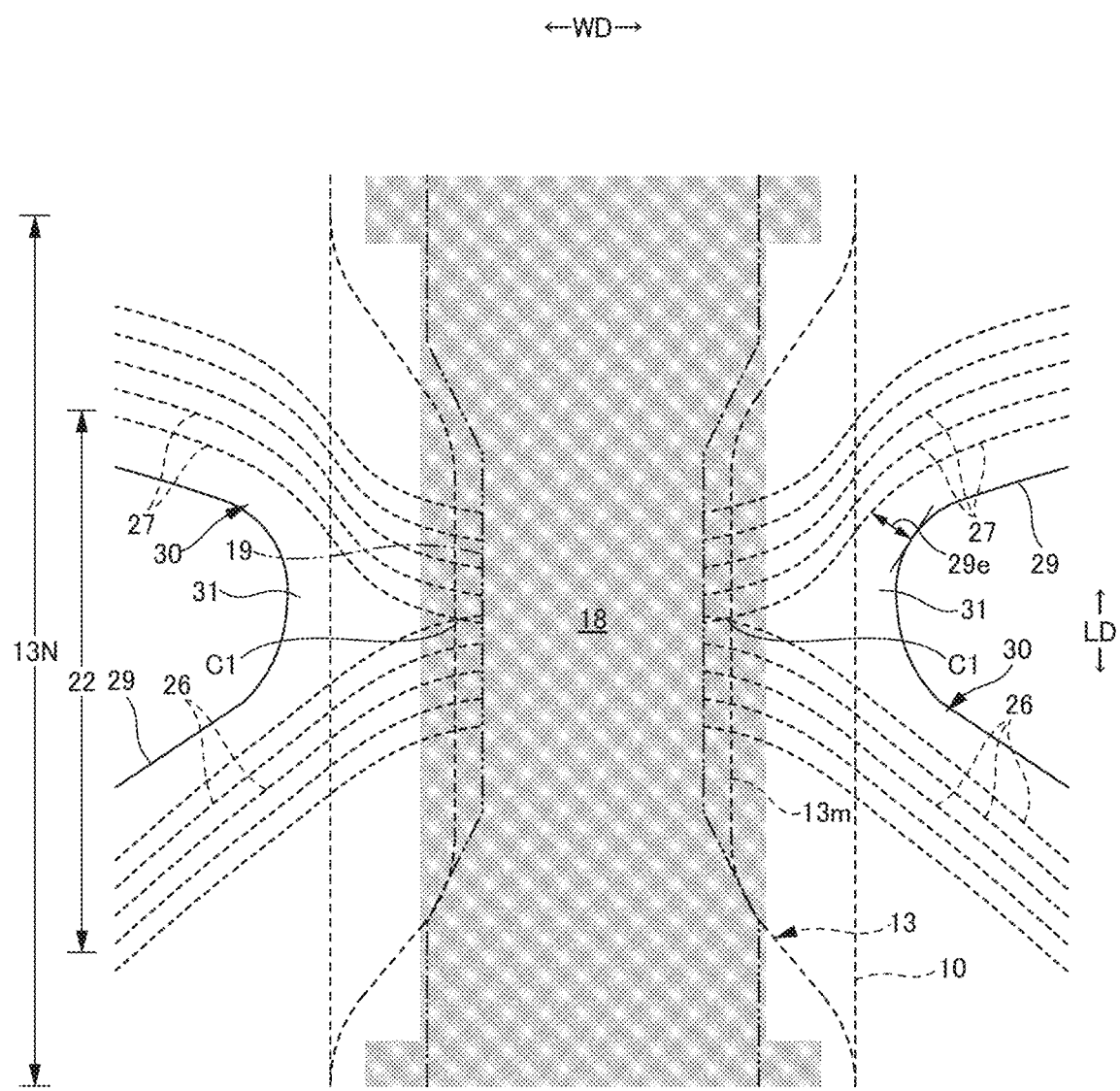
FIG. 11 is an enlarged plan view of a main part of another embodiment.

It is obvious, as illustrated in FIG. 11, it is also possible to make the inner member bonded portion 18 exist to the outside in the width direction WD from the crossing position C1 of the front around-leg elastic member 27 and the back around-leg elastic member 26.

<Explanation of Terms Used Herein>

The following terms in the specification have the following meanings unless otherwise specified in the specification.

"Front body" and "back body" mean front and back portions, respectively, with the center in the front-back direction of a disposable diaper as a boundary.

"Crotch portion" means a portion to be positioned at the crotch of a wearer, in the usual case, as illustrated in FIG. 14, it means the front-back direction range 28 including the center in the front-back direction and in which an acute crossing angle formed by a tangent to the edge 29 of the leg opening in the spread state and the front-back direction is 45° or less.

"Stretch rate" means the value when the natural length is taken as 100%.

"Basis weight" is measured as follows. After preliminary drying a sample or a test piece, the sample or the test piece is left in a test chamber or equipment in the standard state (the test location is at a temperature of 20±5° C. and with a relative humidity of 65% or less) to be constant weight. The preliminary drying refers to making a sample or a test piece constant weight in an environment not exceeding a temperature of 50° C. and a relative humidity of 10 to 25%. For fibers with an official moisture regain of 0.0%, preliminary drying may not be performed. A sample of dimensions of 200 mm×250 mm (±2 mm) is cut using a template for sampling (200 mm×250 mm, ±2 mm) from a test piece in a constant weight. The basis weight is set by weighing the sample, multiplying by 20, and calculating the weight per one square meter.

"Thickness" of an absorber is measured using a thickness measuring instrument (Peacock, large dial gauge type, model J-B (measurement range 0 to 35 mm) or model K-4 (measurement range 0 to 50 mm)) manufactured by OZAKI MFG. CO., LTD., and a sample and the thickness measuring instrument are set to be horizontal.

"Thickness" other than the above is automatically measured under the conditions of a load of 0.098 N/cm$^2$ and a pressing area of 2 cm$^2$ using an automatic thickness measuring device (KES-G5 handy compression measuring program).

"Spread state" means a flatly spread state without shrinkage or slackness.

The dimension and positional relationships of each part means the dimension in the spread state, not the natural length state, unless otherwise stated.

When environmental conditions in tests and measurements are not described, the tests and measurements shall be carried out in a test room or apparatus in a standard state (a temperature of 20±5° C. and a relative humidity of 65% or less at the test location).

INDUSTRIAL APPLICABILITY

The present invention is applicable to a trunks-type disposable diaper as in the above example.

REFERENCE SIGNS LIST 10 inner member
11 top sheet
12 liquid impervious sheet
13 absorber
13N narrower portion
14 package sheet
15 gather sheet
16 gather elastic member
17 diffusion groove
18 inner member bonded portion
19 non-stretchable region
20 outer member
20C folded back portion
21 side seal portion
22 intermediate region
24 waist elastic member
25 lower waist portion elastic member
26 back around-leg elastic member
27 front around-leg elastic member
28 crotch portion
29 edge of leg opening
30 cylindrical leg portion
31 inner thigh contact portion
B back body
BS three-dimensional gather
C1 crossing position
F front body
LD front-back direction
WD width direction

The invention claimed is:

1. A trunks-type disposable diaper comprising:
an outer member having a waist opening and a pair of leg openings and extending from a front waist opening edge to a back waist opening edge;
an inner member provided at least in a crotch portion of the outer member and including an absorber; and
side seal portions that bond both sides on a front side and both sides on a back side of the outer member,
in which the absorber has a narrower portion which is narrower than both front and back sides in an intermediate portion in a front-back direction,
the crotch portion of the outer member has a pair of inner thigh contact portions which respectively extend towards one side and the other side in a width direction from a circumscribed rectangle of the absorber, and
portions along edges of the leg openings including the inner thigh contact portions forms a pair of cylindrical leg portions surrounding root sides of the thighs, the front side of the outer member has one elongated front around-leg elastic member or a plurality of elongated front around-leg elastic members not crossing each other, the elastic member is attached in a pattern of extending from one of the side seal portions toward the center in the width direction along the edge of one of the leg openings, crossing the center in the width direction, extending toward the other leg opening, extending to the other side seal portion along the edge of the other leg opening, the back side of the outer member has one elongated back around-leg elastic member or a plurality of elongated back around-leg elastic members not crossing each other, the elastic member is attached in a pattern of extending from one of the side seal portions toward the center in the width direction along the edge of one of the leg openings, crossing the center in the width direction, extending toward the other leg opening, and extending to the other side seal portion along the edge of the other leg opening, and the front around-leg elastic member and the back around-leg elastic member are attached in a pattern in which at least one front around-leg elastic member and at least one back around-leg elastic member cross each other on both sides in the width direction of an intermediate region that is a region between the edge of one leg opening and the edge of the other leg opening, wherein a crossing position positioned closest to the edge side of the leg opening among the crossing positions of the front around-leg elastic member and the back around-leg elastic member is the same in the width direction position as a side edge of the narrowest part of the narrower portion or located on the further center side in the width direction, and wherein the crotch portion does not have elastic members other than the front around-leg elastic member and the back around-leg elastic member.

2. The trunks-type disposable diaper according to claim 1, wherein the inner member bonded portion that is a region bonding the outer member and the inner member is provided only further to the center side in the width direction than the crossing position of the front around-leg elastic member and the back around-leg elastic member on both sides in the width direction in the intermediate region.

3. The trunks-type disposable diaper according to claim 1, wherein an interval between an edge of the leg opening and an elastic member closest to the edge of the leg opening in a direction orthogonal to a tangent to the edge of the leg opening in the front around-leg elastic member and the back around-leg elastic member is equal to or longer than 10 mm.

4. The trunks-type disposable diaper according to claim 1, wherein a non-stretchable region in which the front around-leg elastic member and the back around-leg elastic member are cut finely is provided further to the center side in the width direction than the crossing position of the front around-leg elastic member and the back around-leg elastic member on both sides in the width direction.

5. The trunks-type disposable diaper according to claim 2, wherein an interval between an edge of the leg opening and an elastic member closest to the edge of the leg opening in a direction orthogonal to a tangent to the edge of the leg opening in the front around-leg elastic member and the back around-leg elastic member is equal to or longer than 10 mm.

6. The trunks-type disposable diaper according to claim 2, wherein a non-stretchable region in which the front around-leg elastic member and the back around-leg elastic member are cut finely is provided further to the center side in the width direction than the crossing position of the front around-leg elastic member and the back around-leg elastic member on both sides in the width direction.

7. The trunks-type disposable diaper according to claim 3, wherein a non-stretchable region in which the front around-leg elastic member and the back around-leg elastic member are cut finely is provided further to the center side in the width direction than the crossing position of the front around-leg elastic member and the back around-leg elastic member on both sides in the width direction.

8. The trunks-type disposable diaper according to claim 1, wherein the inner member bonded portion that is a region bonding the outer member and the inner member is provided only further to the center side in the width direction than all the crossing positions of the front around-leg elastic member and the back around-leg elastic member on both sides in the width direction in the intermediate region.

9. The trunks-type disposable diaper according to claim 1, wherein in a spread state, when a virtual straight line is drawn which extends outward in the width direction and toward the waist side from a virtual point positioned closest to the center side in the width direction on the edge of the leg opening at an angle of 20 degrees with respect to the width direction, on the front side of the outer member, a crossing point between the virtual straight line and the side edge of the outer member in the front-back direction range having the side seal portion is provided, and wherein in the spread state, when a virtual straight line is drawn which extends outward in the width direction and toward the waist side from the virtual point positioned closest to the center side in the width direction on the edge of the leg opening at an angle of 30 degrees with respect to the width direction, on the back side of the outer member, a crossing point between the virtual straight line and the side edge of the outer member in the front-back direction range having the side seal portion is provided.

10. A trunks-type disposable diaper comprising:

an outer member having a waist opening and a pair of leg openings and extending from a front waist opening edge to a back waist opening edge;

an inner member provided at least in a crotch portion of the outer member and including an absorber; and side seal portions that bond both sides on a front side and both sides on a back side of the outer member, in which the absorber has a narrower portion which is narrower than both front and back sides in an intermediate portion in a front-back direction, the crotch portion of the outer member has a pair of inner thigh contact portions which respectively extend towards one side and the other side in a width direction from a circumscribed rectangle of the absorber, and portions along edges of the leg openings including the inner thigh contact portions forms a pair of cylindrical leg portions surrounding root sides of the thighs, the front side of the outer member has one elongated front around-leg elastic member or a plurality of elongated front around-leg elastic member not crossing each other, the elastic member is attached in a pattern of extending from one of the side seal portions toward the center in the width direction along the edge of one of the leg openings, crossing the center in the width direction, extending toward the other leg opening, extending to the other side seal portion along the edge of the other leg opening, the back side of the outer member has one elongated back around-leg elastic member or a plurality of elongated back around-leg elastic members not crossing each other, the elastic member is attached in a pattern of extending from one of the side seal portions toward the center in the width direction along the edge of one of the leg openings, crossing the center in the width direction, extending toward the other leg opening, and extending to the other side seal portion along the edge of the other leg opening, and the front around-leg elastic member and the back around-leg elastic member are attached in a pattern in which at least one front around-leg elastic member and at least one back around-leg elastic member cross each other on both sides in the width direction of an intermediate region that is a region between the edge of one leg opening and the edge of the other leg opening, wherein a crossing position of the front around-leg elastic member and the back around-leg elastic member, positioned closes to the edge side of the leg opening is the same in the width direction position as a side edge of the narrowest part of the narrower portion or located on the further center side in the width direction, wherein the crotch portion does not have elastic members other than the front around-leg elastic member and the back around-leg elastic member, wherein a non-stretchable region in which the front around-leg elastic member and the back around-leg elastic member are cut finely is provided further to the center side in the width direction than the crossing position of the front around-leg elastic member and the back around-leg elastic member on both sides in the width direction, and wherein mutual intervals of the elastic members in a group of the front around-leg elastic members and mutual intervals of the elastic members in a group of the back around-leg elastic members are narrowed toward the center side in the width direction.

\* \* \* \* \*